US007056995B2

United States Patent
Deckers et al.

(10) Patent No.: US 7,056,995 B2
(45) Date of Patent: Jun. 6, 2006

(54) CATALYST SYSTEM FOR THE TRIMERIZATION OF OLEFINS

(75) Inventors: Patrick Jozef Wilhelmus Deckers, Groningen (NL); Bart Hessen, Noordwijk (NL)

(73) Assignee: Stichting Dutch Polymer Institute (NL)

( * ) Notice: Subject to any disclaimer, the term of this patent is extended or adjusted under 35 U.S.C. 154(b) by 169 days.

(21) Appl. No.: 10/645,425

(22) Filed: Aug. 21, 2003

(65) Prior Publication Data

US 2004/0097772 A1 May 20, 2004

Related U.S. Application Data

(63) Continuation-in-part of application No. PCT/NL02/00119, filed on Feb. 22, 2002, which is a continuation-in-part of application No. PCT/NL01/00149, filed on Feb. 22, 2001.

(51) Int. Cl.
*C08F 4/76* (2006.01)
*C08F 4/52* (2006.01)
*C08F 4/64* (2006.01)
*C08F 4/642* (2006.01)

(52) U.S. Cl. ............ 526/160; 526/161; 526/170; 526/172; 526/134; 526/126; 526/144

(58) Field of Classification Search ............ 526/160, 526/170, 943, 352, 103
See application file for complete search history.

(56) References Cited

U.S. PATENT DOCUMENTS 5,043,515 A * 8/1991 Slaugh et al. ............ 585/512

FOREIGN PATENT DOCUMENTS

| EP | 93101111.8 | | 1/1993 |
|---|---|---|---|
| EP | 696 263 B1 | * | 8/1997 |
| WO | 94/25416 | | 11/1994 |
| WO | WO 96/27439 A1 | * | 9/1996 |

OTHER PUBLICATIONS

Saβmannshausen et al. J. Organomet. Chem, 1999, 592, 84-94.*
Flores et al. Organometallics 1996, 15, 4944-4950.*
Lancaster et al. Organometallics 2000, 19, 1599-1608.*
Sassmannshausen J. et al. "Half-Sandwich Complexes of Titanium and Zirconium with Pendant Phenyl Substituents. The Influence of ANSA-ARYL Coordination on the Polymerisation Activity of Half-Sandwich Catalysts". *Journal of Organometallic Chemistry*, vol. 592, 1999, paves 84-94.

* cited by examiner

*Primary Examiner*—David W. Wu
*Assistant Examiner*—Rip A Lee
(74) *Attorney, Agent, or Firm*—Hoffmann & Baron, LLP

(57) ABSTRACT

The invention relates to a catalyst system for the selective trimerization of olefins, which system is based on a titanium complex of formula $(Cp-B(R)_n Ar)TiR^1_3$, wherein:
Cp is a cyclopentadienyl type ligand, optionally substituted,
B is a bridging group, based on a single atom selected from the groups 13 to 16 inclusive of the Periodic System,
Ar is a aromatic group, optionally substituted,
R is, independently, hydrogen, or a hydrocarbon residue, optionally being substituted and optionally containing heteroatoms, or groups R and B are joined together to form a ring,
n is an integer equal to the (valency of B minus 2), and
$R^1$ is a mono-anionic group, and further comprises an activator. The present catalyst system obviates the use of toxic chromium compounds.

15 Claims, No Drawings

CATALYST SYSTEM FOR THE TRIMERIZATION OF OLEFINS

CROSS-REFERENCE TO RELATED APPLICATION

This application is a continuation-in-part of PCT/NL02/00119, filed Feb. 22, 2002, which is a continuation-in-part of PCT/NL01/00149, filed 22 Feb. 2001, both of which are incorporated herein by reference.

FIELD OF INVENTION

The invention relates to a catalyst system for the selective trimerisation of olefins, which system comprises a transition metal complex.

BACKGROUND OF INVENTION

Such a catalyst system for trimerisation of olefins is known from EP-A-0608447 and consists of a combination of a transition metal source, a pyrrole containing compound and a metal alkyl in an electron donor solvent. The transition metal source consists of a chromium, nickel, cobalt, or iron compound, preferably a chromium compound is used.

Because chromium compounds are highly toxic, and therefore need special handling precautions, a catalyst system for the trimerisation of olefins, which is not based on a chromium compound is needed.

SUMMARY OF THE INVENTION

A catalyst system has now been found which is not based on a chromium compound, but still shows a high selectivity in the trimerisation of olefins with respect to the trimerisation product.

DETAILED DESCRIPTION OF THE INVENTION

More specifically, the invention relates to a catalyst system as indicated above, which is characterized in that said catalyst system comprises
a) a half-sandwich substituted cyclopentadienyl titanium complex of formula (Cp-B(R)$_n$Ar)TiR$^1{}_3$ wherein
Cp is a cyclopentadienyl type ligand, optionally substituted,
B is a bridging group, based on a single atom selected from the groups 13 to 16 inclusive of the Periodic System,
Ar is a aromatic group, optionally substituted,
R is, independently, hydrogen, or a hydrocarbon residue, optionally being substituted and optionally containing heteroatoms, or groups R and B are joined together to form a ring,
n is an integer equal to the (valency of B minus 2), and
R$^1$ is a mono-anionic group, and
b) an activator.

It is observed that the catalyst system as disclosed in EP-A-0608447 is preferably a chromium catalyst, but a catalytic system based on a titanium compound, more specifically TiO(acac)$_2$, was also tested as a catalyst for the trimerisation of ethylene. The selectivity for hexene-1 was in that case nevertheless rather low. A high selectivity for hexene-1 is industrially very important because of the use of hexene-1 as starting material for the preparation of different kinds of (co)polymers.

It is further observed that trimerisation is in the above-mentioned reference and in the present disclosure defined as the combination of one or more kinds of olefins, wherein the number of olefin, i.e. double, bonds is reduced by two. The term "trimerisation" is thus intended to include "co-trimerisation". So, for example, the number of olefin bonds in the combination of three ethylene units is reduced by two, to one olefin bond, in 1-hexene.

A half-sandwich substituted cyclopentadienyl titanium complex as a catalyst, in the presence of a co-catalyst, is known for example from Macromol. 1999, 32, 4491–4493. This titanium complex does nevertheless not have a bridging group in its structure; moreover, the catalyst system is used for the synthesis of polyethylenes containing significant amounts of butyl branches, and is thus used in a polymerisation process.

As is known from EP-A-0 780 353, the properties of a polymer do not change markedly with the addition or removal of one or a few repeating units, contrary to the properties of a product obtained by oligomerisation or trimerisation. A polymerisation catalyst thus results in completely different products than a trimerisation catalyst does.

Half-sandwich cyclopentadienyl titanium complexes of formula (CpB(R)$_2$Ar)TiMe$_3$ and (CpB(R)$_2$Ar)TiCl$_3$ are known per se from J. Saβmannshausen et al., J. Organomet. Chem. 1999, 592, 84–94. In these known complexes B(R)$_2$Ar can be CMe$_2$Ph, CHPh$_2$ or SiMe$_2$Ph. These complexes were only used as polymerization catalysts; there is no indication at all that these known catalysts could effectively be used for the selective trimerisation of olefins. On the contrary: it is said that the effect of a comparatively weakly coordinated pendant ligand, such as phenyl, on the behaviour of a polymerisation catalyst is difficult to predict. Moreover, a possible favourable effect of a catalyst having a bridging group only consisting of a single atom, for a trimerisation process of ethene to obtain hexene-1, is not mentioned or suggested in this reference.

As mentioned before, Cp is a cyclopentadienyl type ligand, which is optionally substituted.

More preferably, Cp is a cyclopentadienyl, indenyl or fluorenyl group, which may be substituted or not with one to five (cyclopentadienyl), one to seven (indenyl) or one to nine (fluorenyl) substituent alkyl or silyl groups, especially methyl or trimethylsilyl groups.

In the catalyst system according to the invention Ar is an aromatic group, which is optionally substituted; examples thereof are phenyl, naphthalene, anthracene or phenanthrene. This enumeration is not to be regarded as limitative; other aromatic groups can also be used, provided that a coordination complex, based on π-electrons of said group, together with titanium is present.

As mentioned above, B is a bridging group based on a single atom selected from the groups 13 to 16 inclusive, preferably B, C, N, O, Si, P, S; more preferably C or Si; most preferably C.

In a preferred embodiment of the invention, the catalyst system comprises a complex of the above given formula, wherein the single atom forming the basis of said group B consists of carbon or silicon,
Ar is phenyl, optionally substituted or being part of a larger aromatic entity,
R$^1$ is a halide, or mono-anionic hydrocarbon residue optionally containing heteroatoms, and n is 2, then R is a mono-anionic hydrocarbon residue, optionally containing heteroatoms, or n is 1, then R is a di-anionic hydrocarbon residue, optionally containing heteroatoms.

Expediently, the catalyst system of the invention comprises a titanium complex of the above given formula, wherein Cp is a cyclopentadienyl type ligand being substituted, besides said B-(R)n group, with 1 to 8 groups of formula —YR2R3R4 in which Y is C or Si and R2, R3 and R4 are, independently, H, halogen, lower alkyl, aryl, lower-alkyl-aryl, aryl-lower alkyl residue, wherein said alkyl and aryl are independently substituted or not with one or more lower alkyl residues, said alkyl and aryl residues being independently provided or not with at least one heteroatom, selected from halogen, nitrogen, oxygen, sulphur and phosphor.

It is in this respect observed that by "provided" is to be understood that said heteroatom(s) can be incorporated in the hydrocarbon chain, as well as be present as or in a substituent group.

Expediently, said lower alkyl residues, being the same or different to each other, are linear or branched $C_1$–$C_5$ alkyl residues, more specifically methyl.

In a further preferred embodiment of the present catalyst system, said above mentioned aryl group in the alkyl aryl or aryl alkyl residue is a phenyl group.

Said halogen is preferably fluorine or chlorine.

More preferably the catalyst system of the invention comprises a titanium complex of the above given formula, wherein Ar is a phenyl group, substituted or not at the meta- or para-position(s), B is based on a carbon atom, n is 2, then groups R are, independently, methyl, or ethyl; or n is 1, then group R is =$CH_2$, or forms when R is $C_4H_8$ or $C_5H_{10}$ together with group B a dianionic cyclic group, Cp is $C_5H_4$ or $C_5H_3(SiMe_3)$, and $R^1$ is chlorine, methyl, or benzyl.

The half-sandwich, substituted cyclopentadienyl titanium complex, forming a part of the present catalyst system, is in a preferred embodiment supported by a carrier. This carrier consists expediently either of a metal oxide, which is selected from the group consisting of alumina, boria, magnesia, thoria, zirconia, silica, or mixtures thereof, or it consists of a polymeric material.

As indicated above, the present catalyst system comprises an activator. Said activator is preferably methylalumoxane, a salt of a non-coordinating anion, or a Lewis acid capable of abstracting an anion from said transition metal complex and thus generating a cationic transition metal species with a non-coordinating anion.

An example of a salt of a non-coordinating anion is N,N-dimethylanilinium tetrakis(pentafluorophenyl)borate, while such a Lewis acid is for example $B(C_6F_5)_3$. It is in this respect observed that any activator can be used provided that it is able to generate a cationic transition metal species with a non-coordinating anion. The term "non-coordinating anion" is meant to indicate the anionic part or derivative of the activator, which not or only weakly coordinates to the cationic form of the present catalyst system.

Preferably the activator is methylalumoxane (also known as MAO). The molar ratio of Ti:Al is expediently from 1:100 to 1:1000.

The present catalyst system can further also comprise a scavenger. Examples of a scavenger are i-$Bu_3Al$ and (i-$Bu_2Al)_2O$. A scavenger is normally used to scavenge impurities from a polymerisation medium to obtain a high productivity.

The invention further relates to a process to trimerize olefinic compounds which comprises carrying out said trimerisation in the presence of a catalyst system, as described above, under trimerisation conditions. Such a trimerisation als comprises co-trimerisation according to the definition given before.

The olefin to be trimerized is preferably selected from $C_2$–$C_{20}$ olefins or mixtures of two or more of these olefins. The preferred olefins are ethylene and 1-butene, more preferably ethylene.

The temperature is preferably in the range of from 20–150° C., at a pressure which is commonly in the range from 0,2 to 14 MPa, preferably in the range of from 1,5 to 3 MPa.

The invention will further be explained in the following examples.

EXPERIMENTAL SECTION

General Considerations

All experiments were performed under a nitrogen atmosphere using standard Schlenk and glovebox techniques. Deuterated solvents (Aldrich, Acros) were dried over Na/K alloy and vacuum transferred before use. Cyclooctane (Aldrich, used as internal standard) was distilled from Na prior to use. Toluene (Aldrich, anhydrous, 99,8%) was passed over columns of $Al_2O_3$ (Fluka), BASF R3–11 supported Cu oxygen and molecular sieves (Aldrich, 4 Å). Diethyl ether and THF (Aldrich) were dried over $Al_2O_3$ (Fluka) and the other solvents (Aldrich) were dried over molecular sieves (Aldrich, 4 Å). Ethene (AGA polymer grade) was passed over BASF R3–11 supported Cu oxygen scavenger and molecular sieves (Aldrich, 4 Å).

The compounds 6,6-pentamethylenefulvene, $C_5H_5CH_2Ph$, $(C_5H_4C(=CH_2)Ph)Li$, $(C_5H_4CMe_2Ph)TiCl_3$ (the catalyst used in Example 1), $(C_5H_4SiMe_2Ph)TiCl_3$ (the catalyst used in Example 3), $(C_5H_4CMe_2-3,5-Me_2C_6H_3)TiCl_3$ (the catalyst used in Example 2) and $B(C_6F_5)_3$ were prepared according to procedures known as such. 6,6-Diethylfulvene was prepared analogously to 6,6-pentamethylenefulvene from cyclopentadiene and 3-pentanone. ($C_5H_4CMe_2Ph)TiMe_3$ (used in Examples 10 and 11) was prepared through modification of a known procedure by reaction of $(C_5H_4CMe_2Ph)TiCl_3$ with either $Me_2Mg$ or MeMgI. The preparations of other titanium complexes are disclosed hereafter in the Preparation Examples A to F.

A toluene solution of MAO (26 wt %, Akzo Nobel Chemicals), MAO supported on silica (5 wt %, Witco) and $[PhNMe_2H][B(C_6F_5)_4]$. (Akzo Nobel Chemicals) were used as such.

NMR spectra were recorded on Varian Gemini 200/300 and Unity 500 spectrometers.

The $^1H$ NMR spectra were referenced to resonances of residual protons in the deuterated solvents. Chemicals shifts (δ) are given relative to tetramethylsilane (downfield shifts are positive). GC analyses were performed on a HP 6890 instrument equipped with a HP-1 dimethylpolysiloxane column (19095 z-123). GC-MS analyses were conducted using a HP 5973 mass-selective detector attached to a HP 6890 GC instrument. Elemental analyses are the average of a least two independent determinations.

Preparation Example A

Preparation of $(C_5H_4CH_2Ph)TiCl_3$, to be Used in Example 4.

a) Preparation of $(C_5H_4CH_2Ph)Li$

To a solution of 11.3 mmol n-BuLi in 30 ml of diethyl ether/hexane at −40° C., 1.87 g (12.0 mmol) of CpHCH$_2$Ph [2] was added dropwise. The reaction mixture was allowed to warm to room temperature and stirred overnight. The solvents were removed in vacuo. The white residue was stripped with pentane. After rinsing with 3×10 ml of pentane and after drying in vacuo 1.55 g (9.6 mmol, 85%) of a white solid was isolated.—$^1$H NMR (300 MHz, THF-d$_8$): δ 8.04–7.92 (m, 4H, Ph o- and m-H), 7.82 (m, 1H, Ph p-H), 6.33 (t, $^3J_{HH}$=2.6 Hz, 2H, Cp), 6.29 (t, $^3J_{HH}$=2.6 Hz, 2H, Cp), 4.61 (s, 2H, CH$_2$)—$^{13}$C NMR (75.4 MHz, THF-d$_8$): δ 148.2 (Ph C ipso), 130.5 (Ph o- or m-CH), 129.5 (Ph o- or m-CH), 126.3 (Ph p-CH), 120.0 (Cp C ipso), 105.1 (Cp CH), 103.9 (Cp CH), 39.0 (CH$_2$)

b) Preparation of $(C_5H_4CH_2Ph)TiCl_3$

To a solution of 1.42 g (8.8 mmol) (CpCH$_2$Ph)Li in 40 ml of methylene chloride, cooled at −40° C., 0.96 ml (1.7 g, 8.9 mmol) titanium(IV) chloride was added. The reaction mixture was stirred at ambient temperatures overnight. The methylene chloride was removed in vacuo and the green-brown residue was stripped with pentane. After extraction with toluene, the extract was evaporated in vacuo and the extract residue was dissolved in methylene chloride. Brown crystals were obtained after cooling to −40° C. Yield: 1.58 g (5.1 mmol, 58%)—$^1$H NMR (300 MHz, C$_6$D$_6$): δ 7.09–7.03 (m, 3H, Ph m- and p-H), 6.82 (m, 2H, Ph o-H), 5.98 (m, 4H, Cp), 3.71 (s, 2H, CH$_2$)—$^{13}$C NMR (75.4 MHz, C$_6$D$_6$): δ 142.9, 138.3 (Ph and Cp C ipso), 128.9, 127.2 (Ph CH, one signal overlapped by solvent), 123.6, 123.2 (Cp CH), 37.7 (CH$_2$)—Anal. Calcd for C$_{12}$H$_{11}$TiCl$_3$: C, 46.57; H, 3.58; Ti, 15.48. Found: C, 47.07; H, 3.75, Ti, 15.38.

Preparation Example B

Preparation of $(C_5H_4CEt_2Ph)TiCl_3$, to be Used in Example 5.

a) Preparation of $C_5H_4(TMS)CEt_2Ph$

To a solution of 4.85 g (58 mmol) PhLi in 200 ml of diethyl ether, cooled at −50° C., 8.0 g (60 mmol) of 6,6-diethyl fulvene [1] was added dropwise. The reaction mixture was allowed to warm to room temperature and was stirred for 3 hours. After 3 hours the yellow solution was cooled with an ice bath and 7.6 ml (6.5 g, 60 mmol) of trimethylsilyl chloride was added dropwise. The mixture was allowed to warm to room temperature and stirred overnight. The reaction mixture was poured into 250 ml of ice water. The water layer was extracted with 2×100 ml of light petroleum, after which the combined organic layers were rinsed with 200 ml of brine. The organic phase was dried on MgSO$_4$. After evaporating the low-boiling volatiles in vacuo, the residue was distilled using a Kogelruhr-apparatus. The product distilled at 110° C. at 0.5 mm Hg as a mixture of isomers.

Yield: 9.21 g (32 mmol, 55%)—$^1$H NMR (300 MHz, CDCl$_3$, main isomer): δ 7.28 (m, 4H, Ph o- and m-H), 7.18 (m, 1H, Ph p-H), 6.40 (m, 1H, C$_5$H$_4$), 6.31 (s, 1H, C$_5$H$_4$), 6.22 (m, 1H, C$_5$H$_4$), 3.27 (s, 1H, C$_5$H$_4$), 2.02 (m, 4H, C—CH$_2$—CH$_3$), 0.72 (m, 6H, C—CH$_2$—CH$_3$), 0.06 (s, 9H, TMS)

b) Preparation of $(C_5H_4CEt_2Ph)TiCl_3$

To a solution of 6.30 g (22 mmol) of A.1 in 40 ml of methylene chloride, cooled at −40° C., 2.45 ml (4.2 g, 22 mmol) of titanium chloride was added. The mixture was allowed to warm to room temperature and stirred overnight. The methylene chloride was removed in vacuo and the residue was stripped with pentane. Extraction with methylene chloride and cooling to −60° C. afforded red-brown crystals of the title compound. Yield: 5.63 g (15.3 mmol, 70%)—$^1$H NMR (300 MHz, C$_6$D$_6$): δ 7.24 (d, $^3J_{HH}$=7.3 Hz, 2H, Ph o-H), 7.17 (t, $^3J_{HH}$=7.3 Hz, 2H, Ph m-H), 7.06 (t, $^3J_{HH}$=7.3 Hz, 1H, Ph p-H), 6.26 (t, $^3J_{HH}$=2.8 Hz, 2H, Cp), 6.04 (t, $^3J_{HH}$=2.8 Hz, 2H, Cp), 2.06 (m (dq), 2H, C—CH$_2$—CH$_3$), 1.86 (m (dq), 2H, C—CH$_2$—CH$_3$), 0.51 (t, $^3J_{HH}$=7.3 Hz, 6H, C—CH$_2$—CH$_3$)—$^{13}$C NMR (75.4 MHz, C$_6$D$_6$): δ 154.8 (Ph C ipso), 142.1 (Cp C ipso), 128.8 (Ph o-CH), 128.3 (Ph m-CH, overlap with solvent), 127.2 (Ph p-CH), 123.1, 121.8 (Cp CH), 48.6 (C(C$_2$H$_5$)$_2$ ipso), 29.3 (C—CH$_2$—CH$_3$), 8.5 (C—CH$_2$—CH$_3$)—Anal. Calcd for C$_{16}$H$_{19}$TiCl$_3$: C, 52.57; H, 5.24. Found: C, 52.75; H, 5.27.

Preparation Example C

Preparation of ${CpC[(CH_2)_5]Ph}TiCl_3$, to be Used in Example 6 a) Preparation of $C_5H_4(TMS)C[(CH_2)_5]Ph$

To a solution of 4.00 g (48 mmol) PhLi in 200 ml of diethyl ether, cooled at −50° C., 6.95 g (48 mmol) of 6,6-pentamethylenefulvene [1] was added dropwise. The reaction mixture was allowed to warm to room temperature and was stirred for 3 hours. After 3 hours the yellow solution was cooled with an ice bath and 6.4 ml (5.5 g, 51 mmol) of trimethylsilyl chloride was added dropwise. The mixture was allowed to warm to room temperature and stirred overnight. The reaction mixture was poured into 250 ml of ice water. The water layer was extracted with 2×100 ml of light petroleum, after which the combined organic layers were rinsed with 200 ml of brine. The organic phase was dried on MgSO$_4$. After evaporating the low-boiling volatiles in vacuo, the residue was distilled using a Kogelruhr-apparatus. The product distilled at 165° C. at 0.4 torr as a mixture of isomers. Yield: 8.96 g (30 mmol, 63%)—$^1$H NMR (300 MHz, CDCl$_3$, main isomer): δ 7.40 (m, 2H, Ph O—H), 7.33 (m, 2H, PH m-H), 7.15 (m, 1H, Ph p-H), 6.43 (m, 2H, C$_5$H$_4$), 6.15 (s, 1H, C$_5$H$_4$), 3.27 (s, 1H, C$_5$H$_4$), 2.17 (m, 4H, α-CH$_2$), 1.65–1.40 (m, 6H, β- and γ-CH$_2$), −0.03 (s, 9H, TMS)

b) Preparation of ${C_5H_4C[(CH_2)_5]Ph}TiCl_3$

Titanium chloride (1.4 ml, 2.4 g, 12.7 mmol) was added to a solution of 3.70 g (12.5 mmol) of C$_5$H$_4$(TMS)C[(CH$_2$)$_5$]Ph in 40 ml of methylene chloride, cooled at −40° C. The reaction mixture was allowed to warm to room temperature and was stirred overnight. The methylene chloride was removed in vacuo and the residue was stripped with pentane. The residue was extracted with methylene chloride. Crystallization from a 1:1 mixture of CH$_2$Cl$_2$:pentane afforded red-brown crystals of the desired compound in 78% yield (3.68 g, 9.7 mmol).—$^1$H NMR (300 MHz, C$_6$D$_6$): δ 7.16–7.06 (m, 4H, Ph o- and m-H), 7.01 (m, 1H, Ph p-H), 6.31 (t, $^3J_{HH}$=2.8 Hz, 2H, Cp), 5.97 (t, $^3J_{HH}$=2.8 Hz, 2H, Cp), 2.45 (d, $^2J_{HH}$=13.2 Hz, 2H, α-CH$_2$ (eq)), 1.88 (m, 2H, α-CH$_2$ (ax)), 1.37 (br, 3H, β- and γ-CH$_2$), 1.25–1.05 (m, 3H, β- and γ-CH$_2$)—$^{13}$C NMR (75.4 MHz, C$_6$D$_6$): δ 156.0 (Ph C ipso), 142.1 (Cp C ipso), 129.2 (Ph o-CH), 127.9 (Ph m-CH), 126.8 (Ph p-CH), 123.2, 120.9 (Cp CH), 45.1 ($\underline{C}$[(CH$_2$)$_5$] ipso), 35.8 (α-CH$_2$), 26.1 (γ-CH$_2$), 22.4 (β-CH$_2$)—Anal. Calcd for C$_{17}$H$_{19}$TiCl$_3$: C, 54.08; H, 5.07; Ti, 12.69. Found: C, 53.93; H, 4.90; Ti, 12.62.

Preparation Example D

Preparation of [C$_5$H$_4$C(=CH$_2$)Ph]TiCl$_3$, to be Used in Example 7

To a solution of 0.61 ml (1.06 g, 5.6 mmol) titanium chloride in 40 ml of methylene chloride, cooled at −50° C., 1.80 g (5.6 mmol) [C$_5$H$_4$C(=CH$_2$)Ph]Li was added. The reaction mixture was allowed to warm to room temperature and was stirred overnight. The volatiles were removed in vacuo and the green-black residue was stripped with pentane. Extraction with pentane afforded small analytically pure amounts of the desired compound.—$^1$H NMR (300 MHz, C$_6$D$_6$): δ 7.2–7.05 (m, 5H, Ph), 6.35 (t, $^3J_{HH}$=2.7 Hz, 2H, Cp), 6.01 (t, $^3J_{HH}$=2.7 Hz, 2H, Cp), 5.58 (s, 1H, =CH$_2$), 5.20 (s, 1H, =CH$_2$)— $^{13}$C NMR (75.4 MHz, C$_6$D$_6$): δ 142.5 (Ph C ipso), 139.7 (Cp C ipso), 139.6 ($\underline{C}$(=CH$_2$) ipso), 128.8, 128.7, 128.5 (Ph CH), 123.4, 121.1 (Cp CH), 120.5 (C(=$\underline{CH_2}$))—Anal. Calcd for C$_{13}$H$_{11}$TiCl$_3$: C, 48.57; H, 3.45; Ti, 14.90. Found: C, 48.71; H, 3.55; Ti, 14.78.

Preparation Example E

Preparation of C$_5$H$_3$(3-SiMe$_3$)CMe$_2$Ph]TiCl$_3$, to be Used in Example 8 a) Preparation of C$_5$H$_3$(SiMe$_3$)$_2$CMe$_2$Ph

To a solution of 2.25 g (11.8 mmol) (C$_5$H$_4$CMe$_2$Ph)Li [5] in 50 ml of diethyl ether and 20 ml of THF, cooled in ice water, 1.5 ml (1.3 g, 11.9 mmol) TMSCl was added dropwise. The mixture was allowed to warm to room temperature and was stirred overnight. The yellow solution was cooled in ice water and 4.8 ml (12 mmol) of a 2.5M n-BuLi solution in hexanes was added. After warming up to room temperature the mixture was stirred for 4 hours. The white suspension was cooled in ice water and 1.6 ml (1.4 g, 12.7 mmol) TMSCl was added dropwise. The mixture was allowed to warm to room temperature and stirred overnight. The yellow suspension was poured into 125 ml ice water. The water layer was extracted with 50 ml of light petroleum and the combined organic layers were dried on MgSO$_4$. After evaporation of low-boiling volatiles, the residue was distilled using a Kogelruhr-apparatus. The product distilled at 115° C. at 0.8 Torr. Yield: 2.87 g (8.7 mmol, 74%)—$^1$H NMR (200 MHz, CDCl$_3$): δ 7.4–7.1 (m, 5H, Ph), 6.40 (d, $^3J_{HH}$=2.2 Hz, 2H, Cp), 6.20 (t, $^3J_{HH}$=2.1 Hz, 1H, Cp), 1.53 (s, 6H, CMe$_2$), −0.03 (s, 18H, TMS)

b) Preparation of [C$_5$H$_3$(3-SiMe$_3$)CMe$_2$Ph]TiCl$_3$

To a solution of 0.92 ml (1.6 g, 8.4 mmol) TiCl$_4$ in 50 ml of methylene chloride, cooled at −50° C., 2.75 g (8.4 mmol) of C$_5$H$_3$(SiMe$_3$)$_2$CMe$_2$Ph was added. The reaction mixture was allowed to warm to room temperature and was stirred overnight. The volatiles were removed in vacuo and the residue was stripped with pentane. Extraction with methylene chloride and cooling down to −60° C. afforded 2.76 g (6.7 mmol, 80%) of the desired compound.—$^1$H NMR (300 MHz, C$_6$D$_6$): δ 7.1–6.85 (m, 5H+1H, Ph+Cp), 6.57 (m, 1H, Cp), 6.53 (m, 1H, Cp), 1.63 (s, 6H, CMe$_2$), 0.12 (s, 9H, TMS)—$^{13}$C NMR (75.4 MHz, C$_6$D$_6$): δ 158.5 (Ph C ipso), 148.5 (Cp C ipso), 144.1 (Cp C(TMS) ipso), 128.7, 128.6, 126.7, 126.1, 124.6 (Ph+Cp CH), 41.2 (CMe$_2$ ipso), 29.3, 29.0 (CMe$_2$), −0.8 (TMS)— Anal. Calcd for C$_{17}$H$_{23}$SiTiCl$_3$: C, 49.84; H, 5.66; Ti, 11.69. Found: C, 49.70; H, 5.68; Ti, 11.59.

Preparation Example F

Preparation of [C$_5$H$_3$(3-SiMe$_3$)CMe$_2$-3,5-Me$_2$C$_6$H$_3$]TiCl$_3$, to be Used in Example 9 a) Preparation of C$_5$H$_3$(SiMe$_3$)$_2$CMe$_2$-3,5-Me$_2$C$_6$H$_3$

To a solution of 1.15 g (5.3 mmol) [CpCMe$_2$-3,5-Me$_2$C$_6$H$_3$]Li in 50 ml of diethyl ether, cooled with ice water, 0.7 ml (0.6 g, 5.5 mmol) trimethylsilyl chloride was added dropwise. The reaction mixture was allowed to warm to room temperature and was stirred overnight. The white suspension was cooled to −30° C. and 5.4 mmol of a 2.5M solution of n-BuLi in hexanes was added dropwise. After stirring for 3 hours at ambient temperature, the reaction vessel was placed in ice water and 0.8 ml (0.7 g, 6.4 mmol) trimethylsilyl chloride was added. The reaction mixture was allowed to warm up to room temperature and was stirred overnight. The mixture was poured into 100 ml of ice water. The water layer was extracted twice with 50 ml portions of light petroleum, and the combined organic layers were dried over MgSO$_4$. Kogelruhr-distillation at 160° C. and 0.4 Torr yielded 1.26 g (3.5 mmol, 66%) of the title compound—$^1$H NMR (200 MHz, CDCl$_3$): δ 6.90 (s, 2H, Ar o-H), 6.78 (s, 1H, Ar p-H), 6.37 (m, 2H, Cp), 6.19 (m, 1H, Cp), 2.24 (s, 6H, ArMe), 1.51 (s, 6H, CMe$_2$), −0.05 (s, 18H, TMS)

b) Preparation of [C$_5$H$_3$(3-SiMe$_3$)CMe$_2$-3,5-Me$_2$C$_6$H$_3$]TiCl$_3$

To a solution of 0.35 ml (0.6 g, 3.2 mmol) titanium chloride in 40 ml of methylene chloride, cooled at −40° C., 1.18 g (3.3 mmol) of C$_5$H$_3$(SiMe$_3$)$_2$CMe$_2$-3,5-Me$_2$C$_6$H$_3$ was added dropwise. The reaction mixture was allowed to warm to room temperature and was stirred overnight. The volatiles were removed in vacuo and the residue was stripped with pentane. Extraction with pentane yielded 1.02 g (2.3 mmol, 72%) of light-brown crystals.—$^1$H NMR (300 MHz, C$_6$D$_6$): δ 6.96 (m, 1H, Cp), 6.69 (s, 2H, Ar o-H), 6.64 (m, 1+1H, Cp+p-H), 6.55 (m, 1H, Cp), 2.08 (s, 6H, ArMe), 1.70 (s, 6H, CMe$_2$), 0.13 (s, 9H, TMS)— $^{13}$C NMR (75.4 MHz, C$_6$D$_6$): δ 159.1 (Ar C ipso), 148.5 (Cp C ipso), 144.1 (Cp C(TMS) ipso), 137.9 (Ar m-C ipso), 128.8, 128.4, 127.8, 124.7 (Cp CH+Ar p-CH), 124.1 (Ar m-H), 41.2 (CMe$_2$ ipso), 29.3, 29.2 (CMe$_2$), 21.5 (ArMe), −0.9 (TMS)

Preparation Example G

Preparation of (C$_5$H$_4$CMe$_2$Ph)Ti(CH$_2$Ph)$_3$, to be Used in Example 10

To a stirred solution of 0.52 g of (C$_5$H$_4$CMe$_2$Ph)TiCl$_3$ (1.54 mmol) in 30 ml of diethyl ether, cooled at −40° C., a solution of benzyl magnesium bromide (4.62 mmol) in diethyl ether was added dropwise. The mixture was allowed to warm to room temperature and was stirred for 3 hours. The solvent was removed in vacuo. The red solid was extracted with pentane. Cooling to −40° C. yielded red crystals of the desired product (560 mg, 1.11 mmol, 72%)— $^1$H NMR (500 MHz, C$_6$D$_6$): δ 7.17–7.11 (m, 10H, Ph m- and o-H and Bz m-H), 7.02 (m, 1H, Ph p-H), 6.90 (t, $^3J_{HH}$=7.5 Hz, 3H, Bz p-H), 6.81 (d, $^3J_{HH}$=7.5 Hz, 6H, Bz o-H), 5.74 (ps. t, $^3J_{HH}$=2.8 Hz, 2H, Cp), 5.50 (ps. t, $^3J_{HH}$=2.8 Hz, 2H, Cp), 2.97 (s, 6H, Ti—CH$_2$), 1.38 (s, 6H, CMe$_2$)—$^{13}$C-NMR (125.7 MHz, C$_6$D$_6$): δ 149.6 (s, Ph C ipso), 149.1 (s, Bz C ipso), 146.7 (s, Cp C ipso), 128.8 (dd, $^1J_{CH}$=158 Hz, Bz m-CH, overlap with solvent), 128.5 (d, $^1J_{CH}$=151 Hz, Ph m-CH, overlap with solvent), 127.0 (dm, $^1J_{CH}$=161 Hz, Bz o-CH), 126.5 (dm, $^1J_{CH}$=156 Hz, Ph o-CH), 126.4 (dm, $^1J_{CH}$=156 Hz, Ph p-CH), 123.0 (dt, $^1J_{CH}$=160 Hz, Bz p-CH), 118.4 (dm, $^1J_{CH}$=168 Hz, Cp CH), 113.5 (dm, $^1J_{CH}$=172 Hz, Cp CH), 93.5 (t, $^1J_{CH}$=123 Hz, Ti—CH$_2$), 40.5 (s, CMe$_2$), 30.2 (q, $^1J_{CH}$=122 Hz, CMe$_2$)—Anal. Calcd for C$_{35}$H$_{36}$Ti: C, 83.32; H, 7.19; Ti, 9.49. Found: C, 82.63; H, 7.32; Ti, 9.35.

Preparation Example H

Preparation of [C$_5$H$_3$-1,3-(CMe$_2$Ph)$_2$]TiCl$_3$, to be Used in Example 15 a) Preparation of [C$_5$H$_3$-1,3-(CMe$_2$Ph)$_2$]Li

To a suspension of 2.28 g (27.1 mmol) PhLi in 50 ml of n-hexane, 6.14 g (27.4 mmol) of 3-α,α-dimethylbenzyl-6,6-dimethylfulvene was added. The mixture was refluxed for 5 hours. The precipitate was poured onto a glass frit and rinsed with 2×20 ml of pentane. Drying in vacuo yielded 4.18 g (13.6 mmol, 50%) of the title compound as an off-white solid.—$^1$H NMR (300 MHz, C$_6$D$_6$/THF-d$_8$): δ 7.55 (d, $^3J_{HH}$=8.2 Hz, 4H, Ph o-H), 7.16 (m, 4H, Ph m-H), 7.01 (m, 2H, Ph p-H), 5.87 (m, 1H, Cp), 5.83 (m, 2H, Cp), 1.79 (s, 12H, CMe$_2$)—$^{13}$C NMR (75.4 MHz, C$_6$D$_6$/THF-d$_8$): δ 154.9, 129.0 (Ph and Cp C ipso), 127.8, 126.7, 124.7 (Ph CH), 100.8, 99.8 (Cp CH), 39.8 (CMe$_2$ C ipso), 32.5 (CMe$_2$).

b) Preparation of [η$^5$-C$_5$H$_3$-1,3-(CMe$_2$Ph)$_2$]TiCl$_3$

To a solution of 1.31 g (4.2 mmol) of [C$_5$H$_3$-1,3-(CMe$_2$Ph)$_2$]Li in 30 ml of methylene chloride, cooled at −40° C., 0.47 ml (0.8 g, 4.2 mmol) TiCl$_4$ was added dropwise. The dark brown solution was allowed to warm to room temperature and was stirred overnight. The solvent was removed in vacuo and the residue was stirred with 40 ml of pentane, which was subsequently pumped off. The residue was extracted with 50 ml of toluene, which was replaced by a 1:1 mixture of methylene chloride/pentane (30 ml in total). Cooling to −40° C. afforded 0.22 g (0.5 mmol, 12%) of the title compound.—$^1$H NMR (300 MHz, C$_6$D$_6$): δ 6.98 (m, 2H, Ph p-H), 6.96 (m, 4H, Ph m- or o-H), 6.70 (m, 4H, Ph m- or o-H), 6.50 (m, 1H, Cp), 6.40 (d, $^3J_{HH}$=2.6 Hz, 2H, Cp), 1.60 (s, 6H, CMe$_2$), 1.54 (s, 6H, CMe$_2$)—$^{13}$C NMR (75.4 MHz, C$_6$D$_6$): δ 156.2, 148.8 (Ph and Cp C ipso), 128.4, 126.5, 126.0 (Ph CH), 121.5, 120.5 (Cp CH), 41.7 (CMe$_2$ C ipso), 28.5, 28.4 (CMe$_2$)—Anal. Calcd for C$_{23}$H$_{25}$TiCl$_3$: C, 60.62; H, 5.53. Found: C, 60.16; H, 5.56.

Example 1

Catalytic Ethene Conversion with (C$_5$H$_4$CMe$_2$Ph)TiCl$_3$/MAO

The reactions were performed in a stainless steel 1L autoclave (Medimex), fully temperature and pressure controlled and equipped with solvent and catalyst injection systems. In a typical experiment, the autoclave was evacuated and heated for 45 min at 90° C. prior to use.

The reactor was then brought to the desired temperature, charged with 200 ml of toluene and pressurized with ethene. After equilibrating for 15 min, the appropriate amount of MAO/toluene was injected together with 25 ml of toluene. Subsequently a mixture of 2.50 g cyclooctane (internal standard) and 1.0 ml (0.87 g) of a 15 mM stock solution of the titanium complex in toluene was injected, together with 25 ml of toluene, to start the reaction. During the run the ethene pressure was kept constant to within 0.2 bar of the initial pressure by replenishing flow. After the specified run time, the reactor was vented and the residual MAO was destroyed by addition of 20 ml of ethanol. Samples of the reaction mixture were taken to analyze and quantify the soluble components. Polymeric product was stirred for 90 min in acidified ethanol and repeatedly rinsed with ethanol and light petroleum on a glass frit. The polymer was initially dried in air and subsequently in vacuo at 70° C. overnight.

The results of the catalytic experiments are summarized in Table 1 (ethene conversion with the (C$_5$H$_4$CMe$_2$Ph)TiCl$_3$/MAO catalyst system) and Table 2 (ethene conversion with the (C$_5$H$_4$CMe$_2$Ph)TiCl$_3$/MAO catalyst system).

In these experiments, the C$_6$ fraction consists predominantly of 1-hexene (99+%), with traces of 2- and 3-hexenes. The only detectable product of the C$_8$ fraction is 1-octene. The C$_{10}$ fraction is a mixture of isomers with either vinyl (90%), vinylidene (5%) or internal olefinic (5%) unsaturation, and consists predominantly of 5-methylnon-1-ene (75–85%). Higher olefins (C$_{12}$–C$_{24}$) constitute less than 0.5 wt % of the total amount of product formed.

TABLE 1

| Test nr. | P(ethene) MPa | T ° C. | C$_6$ g (wt %) | C$_8$ g (wt %) | C$_{10}$ g (wt %) | PE g (wt %) | Productivity kg(C$_6$) mol(Ti)$^{-1}$ h$^{-1}$ |
|---|---|---|---|---|---|---|---|
| 1 | 0.2 | 30 | 8.0 (87) | 0.1 (0.8) | 1.0 (11) | 0.2 (1.6) | 1066 |
| 2 | 0.5 | 30 | 20.9 (83) | 0.3 (1.2) | 3.5 (14) | 0.5 (1.8) | 2787 |
| 3 | 1.0 | 30 | 47.2 (86) | 0.9 (1.6) | 5.1 (9) | 1.4 (2.6) | 6292 |
| 4 | 0.5 | 50 | 12.4 (83) | 0.2 (1.1) | 1.6 (11) | 0.7 (4.6) | 1653 |
| 5 | 0.5 | 80 | 3.3 (76) | 0.05 (0.9) | 0.2 (4) | 0.8 (19) | 440 |

Toluene solvent, 15 μmol Ti, Al:Ti = 1000, 30 min run time

TABLE 2

| Test nr. | Run time min | Al:Ti | C$_6$ g (wt %) | C$_8$ g (wt %) | C$_{10}$ g (wt %) | PE g (wt %) | Productivity kg(C$_6$) mol(Ti)$^{-1}$ h$^{-1}$ |
|---|---|---|---|---|---|---|---|
| 6 | 15 | 1000 | 16.6 (89) | 0.2 (1.0) | 1.4 (8) | 0.4 (2.2) | 4413 |
| 7 | 30 | 1000 | 20.9 (83) | 0.3 (1.2) | 3.5 (14) | 0.5 (1.8) | 2787 |

TABLE 2-continued

| Test nr. | Run time min | Al:Ti | $C_6$ g (wt %) | $C_8$ g (wt %) | $C_{10}$ g (wt %) | PE g (wt %) | Productivity $kg(C_6)$ $mol(Ti)^{-1} h^{-1}$ |
|---|---|---|---|---|---|---|---|
| 8 | 60 | 1000 | 27.1 (80) | 0.4 (1.2) | 5.5 (16) | 0.9 (2.7) | 1809 |
| 9 | 30 | 500 | 15.2 (86) | 0.2 (1.2) | 1.8 (10) | 0.5 (2.8) | 2029 |

Toluene solvent, 15 μmol Ti, 30 °C., 0.5 MPa ethene

Comparative Example A

Catalytic Ethene Conversion with ($C_5H_4CMe_3$)$TiCl_3$/MAO

The general procedure and conditions of example 1 were followed, using the ($C_5H_4CMe_3$)$TiCl_3$/MAO catalyst system. The results of the catalytic experiment are listed in Table 3.

TABLE 3

| Test nr. | P(ethene) MPa | T °C. | $C_6$ g (wt %) | $C_8$ g (wt %) | $C_{10}$ g (wt %) | PE g (wt %) | Productivity $kg(C_6)$ $mol(Ti)^{-1} h^{-1}$ |
|---|---|---|---|---|---|---|---|
| a | 0.5 | 30 | 0.5 (17) | 0.1 (3) | 0.1 (4) | 2.4 (76) | 72 |

Example 2

Catalytic Ethene Conversion with ($C_5H_4CMe_2$-3,5$Me_2C_6H_3$)$TiCl_3$/MAO

The general procedure and conditions of example 1 were followed, using the ($C_5H_4CMe_2$-3,5-$Me_2C_6H_3$)$TiCl_3$/MAO catalyst system. The results of the catalytic experiments are listed in Table 4.

TABLE 4

| Test nr. | P(ethene) MPa | T °C. | $C_6$ g (wt %) | $C_8$ g (wt %) | $C_{10}$ g (wt %) | PE g (wt %) | Productivity $kg(C_6)$ $mol(Ti)^{-1} h^{-1}$ |
|---|---|---|---|---|---|---|---|
| 10 | 0.5 | 30 | 7.9 (94) | 0.02 (0.2) | 0.4 (5) | 0.1 (1.3) | 1052 |
| 11 | 0.5 | 50 | 4.5 (93) | 0.03 (0.6) | 0.2 (4) | 0.1 (2.1) | 599 |

Example 3

Catalytic Ethene Conversion with ($C_5H_4SiMe_2Ph$)$TiCl_3$/MAO

The general procedure and conditions of example 1 were followed, using the ($C_5H_4SiMe_2Ph$)$TiCl_3$/MAO catalyst system. The results of the catalytic experiments are listed in Table 5. Higher olefins ($C_{12}$–$C_{24}$) are also formed, constituting about 8 wt % of the total amount of product formed.

TABLE 5

| Test nr. | P(ethene) MPa | T °C. | $C_6$ g (wt %) | $C_8$ g (wt %) | $C_{10}$ g (wt %) | $C_{12}$–$C_{24}$ g (wt %) | PE g (wt %) | Productivity $kg(C_6)$ $mol(Ti)^{-1} h^{-1}$ |
|---|---|---|---|---|---|---|---|---|
| 12 | 0.5 | 30 | 2.1 (36) | 0.3 (5) | 0.4 (7) | 0.5 (8) | 2.6 (44) | 284 |
| 13 | 0.5 | 50 | 2.6 (47) | 0.4 (7) | 0.4 (7) | 0.4 (7) | 1.7 (32) | 352 |

Example 4

Catalytic Ethene Conversion with $(C_5H_4CH_2Ph)TiCl_3$/MAO

The general procedure and conditions of example 1 were followed, using the $(C_5H_4CH_2Ph)TiCl_3$/MAO catalyst system. The results of the catalytic experiments are listed in Table 6. Higher olefins ($C_{12}$–$C_{24}$) are also formed, constituting about 9 wt % of the total amount of products formed.

TABLE 6

| Test nr. | P(ethene) MPa | T °C. | $C_6$ g (wt %) | $C_8$ g (wt %) | $C_{10}$ g (wt %) | $C_{12}$–$C_{24}$ g (wt %) | PE g (wt %) | Productivity kg($C_6$) mol(Ti)$^{-1}$ h$^{-1}$ |
|---|---|---|---|---|---|---|---|---|
| 14 | 0.5 | 30 | 2.7 (42) | 0.4 (6) | 0.6 (9) | 0.6 (9) | 2.2 (34) | 361 |
| 15 | 0.5 | 50 | 3.0 (54) | 0.3 (6) | 0.5 (9) | 0.5 (9) | 1.2 (22) | 405 |

Example 5

Catalytic Ethene Conversion with $(C_5H_4CEt_2Ph)TiCl_3$/MAO

The general procedure and conditions of example 1 were followed, using the $(C_5H_4CEt_2Ph)TiCl_3$/MAO catalyst system. The results of the catalytic experiments are listed in Table 7.

TABLE 7

| Test nr. | P(ethene) MPa | T °C. | $C_6$ g (wt %) | $C_8$ g (wt %) | $C_{10}$ g (wt %) | PE g (wt %) | Productivity kg($C_6$) mol(Ti)$^{-1}$ h$^{-1}$ |
|---|---|---|---|---|---|---|---|
| 16 | 0.5 | 30 | 18.5 (88) | 0.05 (0.3) | 1.4 (7) | 1.0 (4.6) | 2462 |
| 17 | 0.5 | 50 | 8.7 (84) | 0.03 (0.3) | 0.6 (5) | 1.0 (9.9) | 1159 |

Example 6

Catalytic Ethene Conversion with $\{CpC[(CH_2)_5]Ph\}TiCl_3$/MAO

The general procedure and conditions of example 1 were followed, using the $\{C_5H_4C[(CH_2)_5]Ph\}TiCl_3$/MAO catalyst system. The results of the catalytic experiments are listed in Table 8.

TABLE 8

| Test nr. | P(ethene) MPa | T °C. | $C_6$ g (wt %) | $C_8$ g (wt %) | $C_{10}$ g (wt %) | PE g (wt %) | Productivity kg($C_6$) mol(Ti)$^{-1}$ h$^{-1}$ |
|---|---|---|---|---|---|---|---|
| 18 | 0.5* | 30 | 24.4 (87) | 0.1 (0.3) | 2.9 (10) | 0.6 (2.0) | 3248 |
| 19 | 0.5* | 50 | 12.0 (86) | 0.1 (0.4) | 1.2 (9) | 0.7 (5.2) | 1593 |
| 20 | 0.5** | 30 | 16.4 (91) | 0.04 (0.2) | 1.4 (8) | 0.2 (1.3) | 4362 |

*30 min run time,

**15 min run time

Example 7

Catalytic Ethene Conversion with [$C_5H_4C(=CH_2)$Ph]TiCl$_3$/MAO

The general procedure of example 1 was followed, using the [$C_5H_4C(=CH_2)$Ph]TiCl$_3$/MAO catalyst system. The conditions and results of the catalytic experiments are listed in Table 9.

TABLE 9

Catalytic ethene conversion with the [$C_5H_4C(=CH_2)$Ph]TiCl$_3$/MAO system (toluene solvent, 15 μmol Ti, Al:Ti = 1000, 30 min run time)

| Test nr. | P(ethene) MPa | T °C. | $C_6$ g (wt %) | $C_8$ g (wt %) | $C_{10}$ g (wt %) | PE g (wt %) | Productivity kg($C_6$) mol(Ti)$^{-1}$ h$^{-1}$ |
|---|---|---|---|---|---|---|---|
| 21 | 0.5 | 30 | 17.3 (88) | 0.1 (0.3) | 1.4 (7) | 0.9 (4.7) | 2307 |
| 22 | 0.5 | 50 | 10.9 (86) | 0.03 (0.2) | 0.7 (6) | 1.1 (8.3) | 1449 |

Example 8

Catalytic Ethene Conversion with [$C_5H_3(3-SiMe_3)$CMe$_2$Ph]TiCl$_3$/MAO

The general procedure and condictions of example 1 were followed, using the [$C_5H_3(3-SiMe_3)$CMe$_2$Ph]TiCl$_3$/MAO catalyst system. The results of the catalytic experiments are listed in Table 10.

TABLE 10

| Test nr. | P(ethene) MPa | T °C. | $C_6$ g (wt %) | $C_8$ g (wt %) | $C_{10}$ g (wt %) | PE g (wt %) | Productivity kg($C_6$) mol(Ti)$^{-1}$ h$^{-1}$ |
|---|---|---|---|---|---|---|---|
| 23 | 0.5 | 30 | 25.2 (85) | 0.6 (2.1) | 3.3 (11) | 0.4 (1.2) | 3357 |
| 24 | 0.5 | 50 | 20.1 (84) | 0.4 (1.5) | 3.3 (14) | 0.3 (1.3) | 2683 |
| 25 | 0.5 | 80 | 8.0 (88) | 0.1 (1.4) | 0.8 (8) | 0.2 (2.1) | 1069 |

Example 9

Catalytic Ethene Conversion with [$C_5H_3(3-SiMe_3)$CMe$_2$-3,5-Me$_2$C$_6$H$_3$]TiCl$_3$/MAO The general procedure and conditions of example 1 were followed, using the [Cp(TMS)CMe$_2$-3,5-Me$_2$C$_6$H$_3$]TiCl$_3$/MAO catalyst system. The results of the catalytic experiments are listed in Table 11. For the run at 30° C., the $C_6$ fraction consists of 99.9% 1-hexene, and the $C_{10}$ fraction of 94% 5-methylnon-1-ene.

TABLE 11

| Test nr. | P (ethene) MPa | T °C. | $C_6$ g (wt %) | $C_8$ g (wt %) | $C_{10}$ g (wt %) | PE g (wt %) | Productivity kg($C_6$) mol (Ti)$^{-1}$ h$^{-1}$ |
|---|---|---|---|---|---|---|---|
| 26 | 0.5 | 30 | 40.1 (84) | 0.1 (0.2) | 7.0 (15) | 0.3 (0.6) | 5347 |
| 27 | 0.5 | 50 | 25.7 (82) | 0.1 (0.3) | 4.8 (15) | 0.6 (1.9) | 3427 |

Example 10

Catalytic Ethene Conversion with ($C_5H_4$CMe$_2$Ph)Ti(CH$_2$Ph)$_3$/MAO

The general procedure and conditions of example 1 were followed, using the ($C_5H_4$CMe$_2$Ph)Ti(CH$_2$Ph)$_3$/MAO catalyst system. The results of the catalytic experiments are listed in Table 12.

TABLE 12

| Test nr. | P (ethene) MPa | T °C. | $C_6$ g (wt %) | $C_8$ g (wt %) | $C_{10}$ g (wt %) | PE g (wt %) | Producti- vity kg($C_6$) mol (Ti)$^{-1}$ h$^{-1}$ |
|---|---|---|---|---|---|---|---|
| 28 | 0.5 | 30 | 23.8 (82) | 0.3 (1.1) | 4.6 (16) | 0.5 (1.6) | 3175 |
| 29 | 0.5 | 50 | 18.6 (78) | 0.3 (1.1) | 4.0 (17) | 0.8 (3.3) | 2480 |

Example 11

Catalytic Ethene Conversion with $(C_5H_4CMe_2Ph)$ $TiMe_3$/MAO

The general procedure and conditions of example 1 were followed, using the $(C_5H_4CMe_2Ph)TiMe_3$/MAO catalyst system. The results of the catalytic experiment are listed in Table 13.

TABLE 13

| Test nr. | P (ethene) MPa | T °C. | $C_6$ g (wt %) | $C_8$ g (wt %) | $C_{10}$ g (wt %) | PE g (wt %) | Productivity kg($C_6$) mol $(Ti)^{-1}$ $h^{-1}$ |
|---|---|---|---|---|---|---|---|
| 30 | 0.5 | 30 | 25.7 (81) | 0.4 (1.2) | 5.2 (16) | 0.5 (1.5) | 3428 |
| 31 | 0.5 | 50 | 18.1 (79) | 0.2 (1.0) | 3.8 (17) | 0.7 (3.2) | 2412 |

Example 12

Catalytic Ethene Conversion with $(C_5H_4CMe_2Ph)$ $TiMe_3$/MAO/$SiO_2$

The reaction was performed in a stainless steel 1 l autoclave (Medimex), fully temperature and pressure controlled and equipped with solvent and catalyst injection systems. Prior to use the autoclave was preheated in vacuo for 45 min at 90° C. The reactor was cooled to 30° C., charged with 200 ml of toluene and pressurized with ethene. After equilibrating for 15 min, a slurry of 2.05 g of 5 wt % MAO/$SiO_2$ in 10 ml of toluene was injected together with 30 ml of toluene. Subsequently a mixture of 2.50 g cyclooctane (internal standard) and 1.0 ml (0.87 g) of a 15 mM stock solution of $(C_5H_4CMe_2Ph)TiMe_3$ in toluene was injected, together with 25 ml of toluene, to start the reaction. During reaction the ethene pressure was kept constant to within 0.2 bar of the initial pressure by replenishing flow. After 30 min the reactor was vented and the remaining residual MAO was destroyed by addition of 20 ml of ethanol. Samples of the reaction mixture were taken to analyze and quantify the soluble components. The solids (polyethene and silica support) were stirred in acidified ethanol for 90 min and rinsed repeatedly with ethanol and light petroleum on a glass frit. The material was dried in air overnight and subsequently in vacuo at 70° C. overnight, yielding 1.7 g of which the polyethene fraction was not determined. The results of the catalytic experiment are listed in Table 14; the conditions were: toluene solvent, 15 µmol Ti, Al:Ti=250, 30 min run time. Weight percentages calculated on $C_6$–$C_{10}$ products only.

татle 14

| Test nr. | P (ethene) MPa | T °C. | $C_6$ g (wt %) | $C_8$ g (wt %) | $C_{10}$ g (wt %) | PE g (wt %) | Productivity kg($C_6$) mol $(Ti)^{-1}$ $h^{-1}$ |
|---|---|---|---|---|---|---|---|
| 32 | 0.5 | 30 | 13.8 (95) | 0.1 (0.8) | 0.6 (4) | n.d. | 1837 |

Example 13

Catalytic Ethene Conversion with $(C_5H_4CMe_2Ph)$ $TiMe_3$/$[PhNMe_2H][B(C_6F_5)_4]$ The reactions were performed in a stainless steel 500 mL autoclave (Medimex), fully temperature and pressure controlled and equipped with solvent and catalyst injection systems. Prior to use the autoclave was preheated in vacuo for 45 min at 90° C. The reactor was cooled to the desired temperature, charged with 150 ml of toluene and pressurized with ethene. After equilibrating for 15 min, a suspension of 16.5 µmol $(PhNMe_2H)$ $[B(C_6F_5)_4]$ in 5 ml of toluene was injected together with 25 ml of toluene. Subsequently a mixture of 2.50 g cyclooctane (internal standard) and 1.0 ml (0.87 g) of a 15 mM stock solution of the titanium trimethyl complex in toluene was injected, together with 25 ml of toluene, to start the reaction. During reaction the ethene pressure was kept constant to within 0.2 bar of the initial pressure by replenishing flow. After the desired run time, the reactor was vented and samples of the reaction mixture were taken to analyze and quantify the soluble components. The polymer was repeatedly rinsed with ethanol and light petroleum on a glass frit. The polymer was dried in air overnight and subsequently dried in vacuo at 70° C. overnight. The results of the catalytic experiments are listed in Table 15. The conditions were: toluene solvent, 15 µmol Ti, B:Ti=1.1, 30 min run time

TABLE 15

| Test nr. | P (ethene) MPa | T °C. | $C_6$ g (wt %) | $C_8$ g (wt %) | $C_{10}$ g (wt %) | PE g (wt %) | Productivity kg($C_6$) mol $(Ti)^{-1}$ $h^{-1}$ |
|---|---|---|---|---|---|---|---|
| 33 | 0.5 | 30 | 14.6 (90) | 0.2 (1.3) | 1.2 (7) | 0.3 (2.0) | 1948 |
| 34 | 0.5 | 50 | 14.0 (82) | 0.2 (1.1) | 2.2 (13) | 0.6 (3.4) | 1867 |

Example 14

Catalytic Ethene Conversion with $(C_5H_4CMe_2Ph)$ $TiMe_3$/$B(C_6F_5)_3$

The reaction was performed in a stainless steel 500 mL autoclave (Medimex), fully temperature and pressure controlled and equipped with solvent and catalyst injection systems. Prior to use the autoclave was preheated in vacuo for 45 min at 90° C. The reactor was cooled to the desired temperature, charged with 150 ml of toluene and pressurized with ethene. After equilibrating for 15 min, 1.0 ml (0.87 g) of a 16.5 mM stock solution of $B(C_6F_5)_3$ in toluene was injected together with 25 ml of toluene. Subsequently a mixture of 2.50 g cyclooctane (internal standard) and 1.0 ml (0.87 g) of a 15 mM stock solution of the titanium trimethyl complex in toluene was injected, together with 25 ml of toluene, to start the reaction. During reaction the ethene pressure was kept constant to within 0.2 bar of the initial pressure by replenishing flow. After the desired run time, the reactor was vented and samples of the reaction mixture were taken to analyze and quantify the soluble components. The polymer was repeatedly rinsed with ethanol and light petroleum on a glass frit. The polymer was dried in air overnight and subsequently dried in vacuo at 70° C. overnight. The results of the catalytic experiment are listed in Table 16. The conditions were: toluene solvent, 15 μmol Ti, B:Ti=1.1, 30 min run time.

TABLE 16

| Test nr. | P (ethene) MPa | T °C. | $C_6$ g (wt %) | $C_8$ g (wt %) | $C_{10}$ g (wt %) | PE g (wt %) | Productivity kg($C_6$) mol (Ti)$^{-1}$ h$^{-1}$ |
|---|---|---|---|---|---|---|---|
| 35 | 0.5 | 30 | 5.8 (88) | 0.1 (0.9) | 0.3 (5) | 0.4 (6.6) | 776 |

Example 15

Catalytic Ethene Conversions with [$C_5H_3$-1,3-($CMe_2Ph$)$_2$Ph)$_2$]TiCl$_3$/MAO The general procedure and conditions of example 1 were followed, using the [$C_5H_3$-1,3-($CMe_2Ph$)$_2$]TiCl$_3$/MAO catalyst system. The results of the catalytic experiments are listed in Table 17.

TABLE 17

| Test nr. | P (ethene) MPa | T °C. | Run time min | $C_6$ g (wt %) | $C_{10}$ g (wt %) | PE g (wt %) | Productivity kg($C_6$) mol (Ti)$^{-1}$ h$^{-1}$ |
|---|---|---|---|---|---|---|---|
| 36 | 0.5 | 30 | 30 | 11.9 (91) | 0.6 (5) | 0.3 (2.3) | 1575 |
| 37 | 0.5 | 30 | 120 | 46.6 (89) | 4.1 (8) | 0.8 (1.5) | 1550 |

What is claimed is:

1. A process for the selective trimerization of olefinic compounds under trimerization conditions in the presence of a catalyst system, said process comprising the steps of:
   A) providing a catalyst system comprising:
      a) a cyclopentadienyl titanium complex of formula (Cp-B(R)$_n$Ar)TiR$^1_3$

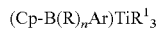

wherein
      Cp is a cyclopentadienyl type ligand, or cyclopentadienyl type ligand being substituted,
      B is a bridging group, based on a single atom selected from the groups 13 to 16 inclusive of the Periodic System,
      Ar is an aromatic group, or a substituted aromatic group,
      R is, independently, hydrogen, a hydrocarbon residue, a hydrocarbon being substituted, or a hydrocarbon containing heteroatams, or groups R and B are joined together to form a ring,
      n is an integer equal to the valency of B minus 2, and
      R$^1$ is a mono-anionic group, and
   b) an activator;
   B) providing olefinic compounds, wherein said olefinic compounds are selected from the group consisting of $C_2$–$C_{20}$ olefins and mixtures of two or more of these olefins; and
   C) trimerizing said olefinic compounds in the presence of said catalyst system, wherein said process is effected at a pressure from 0.2 to 14 MPa.

2. The process according to claim 1, wherein said process is effected at a temperature from 20–150° C.

3. The process according to claim 1, wherein the single atom of B is selected from the group consisting of B, C, N, O, Si, P and S.

4. The process according to claim 1 wherein
   B is carbon or silicon;
   Ar is phenyl, optionally substituted or being part of a larger aromatic entity;
   R$^1$ is a halogen atom, mono-anionic hydrocarbon residue, mono-anionic hydrocarbon residue containing heteroatoms, and combinations thereof; and
   n is 1 or 2, where n is 2, R is a mono-anionic hydrocarbon residue, mono-anionic hydrocarbon residue containing heteroatoms, and combinations thereof; and where n is 1, R is a di-anionic hydrocarbon residue, or a di-anionic hydrocarbon residue containing heteroatoms.

5. The process according to claim 1, wherein Cp is a cyclopentadienyl type ligand being substituted, besides said B-(R)$_n$ group, with 1 to 8 groups of formula —YR2R3R4 in which Y is C or Si and R2, R3 and R4 are, independently, H, halogen, lower alkyl, aryl, lower-alkyl-aryl, aryl-lower alkyl residue, wherein said alkyl and aryl are independently substituted or not with one or more lower alkyl residues, said alkyl and aryl residues being independently provided or not with at least one heteroatom, selected from the group consisting of halogen, nitrogen, oxygen, sulfur and phosphor.

6. The process according to claim 5, wherein said lower alkyl residues, being the same or different to each other, are linear or branched $C_1$–$C_5$ alkyl residues.

7. The process according to claim 5, wherein said aryl group in the lower-alkyl-aryl or aryl-lower-alkyl residue is a phenyl group.

8. The process according to claim 4, wherein said halogen is fluorine or chlorine.

9. The process according to claim 5, wherein
   Ar is a phenyl group, substituted or not at the meta- or para-position;
   B is based on a carbon atom;
   n is 1 or 2, where n is 2, R is, independently, methyl, or ethyl; and where n is 1, R is =CH$_2$, or forms when R is $C_4H_8$ or $C_5H_{10}$ together with group B a cyclic structure;
   Cp is $C_5H_4$ or $C_5H_3$(SiMe$_3$), or $C_5H_3$(CMe$_2$Ph); and
   R$^1$ is chlorine, methyl, or benzyl.

10. The process according to claim 5, wherein said titanium complex is supported on a carrier.

11. The process according to claim 5, wherein said activator is methylalumoxane, a salt of a non-coordinating anion, or a Lewis acid generating a cationic transition metal species with a non-coordinating anion.

12. The process according to claim 11 wherein the activator is methylalumoxane and the molar ratio of Ti:Al is from 1:100 to 1:1000.

13. The process according to claim 5 wherein said catalyst system further comprises a scavenger.

14. The process according to claim 13, wherein said scavenger is selected from the group consisting of i-Bu$_3$Al and (i-Bu$_2$Al)$_2$O.

15. The process according to claim 2, wherein said process is effected at a pressure from 1.5 to 3 MPa.

* * * * *